United States Patent
Farri et al.

(10) Patent No.: US 11,449,143 B2
(45) Date of Patent: Sep. 20, 2022

(54) HAPTIC INPUT TEXT GENERATION

(71) Applicant: KONINKLIJKE PHILIPS N.V., Eindhoven (NL)

(72) Inventors: Oladimeji Feyisetan Farri, Yorktown Heights, NY (US); Junyi Liu, Windham, NH (US); Sheikh Sadid Al Hasan, Cambridge, MA (US); Vivek Varma Datla, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/979,199

(22) PCT Filed: Jun. 11, 2019

(86) PCT No.: PCT/EP2019/065113
§ 371 (c)(1),
(2) Date: Sep. 9, 2020

(87) PCT Pub. No.: WO2019/238623
PCT Pub. Date: Dec. 19, 2019

(65) Prior Publication Data
US 2021/0357031 A1    Nov. 18, 2021

Related U.S. Application Data

(60) Provisional application No. 62/683,285, filed on Jun. 11, 2018.

(51) Int. Cl.
*G06F 3/01* (2006.01)
*G16H 10/60* (2018.01)
*G06F 40/56* (2020.01)
*G06N 3/04* (2006.01)

(52) U.S. Cl.
CPC .............. *G06F 3/016* (2013.01); *G06F 3/014* (2013.01); *G06F 40/56* (2020.01); *G06N 3/0454* (2013.01); *G16H 10/60* (2018.01)

(58) Field of Classification Search
CPC .......... G06F 3/016; G06F 40/56; G06F 3/014; G16H 10/60
See application file for complete search history.

(56) References Cited

U.S. PATENT DOCUMENTS

| | | | |
|---|---|---|---|
| 2010/0134327 A1 | 6/2010 | Ceruti et al. | |
| 2010/0274447 A1* | 10/2010 | Stumpf | G01D 15/00 73/146 |
| 2011/0148794 A1 | 6/2011 | Cohen et al. | |

(Continued)

FOREIGN PATENT DOCUMENTS

| | | | |
|---|---|---|---|
| JP | 2016105248 A2 | 6/2016 | |
| WO | 2004114107 A1 | 12/2004 | |

OTHER PUBLICATIONS

PCT/EP2019/065113 International Search Report dated Jun. 11, 2019.

*Primary Examiner* — David E Choi (57) ABSTRACT

Methods and systems for generating text from a haptic-based input. The system may include an interface for receiving a haptic-based input and a processor executing instructions stored on a memory and providing a model. The model is configured to at least receive the haptic-based input and supply a text describing the haptic-based input using the interface.

20 Claims, 6 Drawing Sheets

(56) References Cited

U.S. PATENT DOCUMENTS

| | | | | |
|---|---|---|---|---|
| 2014/0178642 A1* | 6/2014 | Milanovska | ............ | F24C 15/10 |
| | | | | 428/149 |
| 2016/0015272 A1* | 1/2016 | Gaddipati | ............ | A61B 5/4827 |
| | | | | 600/587 |
| 2017/0285774 A1* | 10/2017 | Parikh | ..................... | G06F 3/167 |
| 2018/0121419 A1* | 5/2018 | Lee | ......................... | G06F 40/30 |
| 2019/0303473 A1* | 10/2019 | Sen | ................... | G06F 16/24522 |
| 2021/0029112 A1* | 1/2021 | Palle | ....................... | G06F 21/32 |
| 2021/0357031 A1* | 11/2021 | Farri | ...................... | G06F 3/016 |

* cited by examiner

HAPTIC INPUT TEXT GENERATION

CROSS-REFERENCE TO PRIOR APPLICATIONS

This application is the U.S. National Phase application under 35 U.S.C. § 371 of International Application No. PCT/EP2019/065113, filed on Jun. 11, 2019, which claims the benefit of U.S. Patent Application No. 62/683,285, filed on Jun. 11, 2018. These applications are hereby incorporated by reference herein.

TECHNICAL FIELD

Embodiments described herein generally relate to systems and methods for generating text and, more particularly but not exclusively, to systems and methods for generating text from haptic-based input.

BACKGROUND

The physical examination (PE) phase of a typical clinician-patient interaction relies heavily on tactile feedback. Specifically, palpation is an integral part of PE and involves the clinician's synthesis of the geometric and textual properties of the patient's body as the clinician touches the skin covering particular body areas. Towards the end of the clinician-patient interaction, findings from the palpation that may help the clinician establish a working diagnosis must be documented in the patient's electronic health record (EHR).

However, documenting the PE is usually a time-consuming process. Furthermore, it poses a challenge to the clinician's cognitive abilities as the details from the clinical palpation have to be recollected in the event of a time gap between the PE and when the physician is ready to document in the EHR. Reliance on the clinician's memory could increase the risk of misrepresentation of findings during the PE, and such mistakes could have an adverse impact on the quality of care that the patient receives.

A need exists, therefore, for methods and systems that overcome the above disadvantages of existing PE documentation techniques.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

In one aspect, embodiments relate to a method for generating text from a haptic-based input. The method includes gathering a haptic-based input using at least one sensor device, providing the haptic-based input to a processor executing instructions stored on a memory and providing a model, and receiving, using an interface, a text from the model describing the gathered haptic-based input.

In some embodiments, the haptic-based input is representative of a palpation examination. In some embodiments, the received text describes a finding of the palpation examination.

In some embodiments, the at least one sensor device is configured as part of a glove worn by a user.

In some embodiments, the method further includes providing previously-gathered haptic-based inputs and at least one sentence associated with each of the previously-gathered haptic-based inputs to the processor executing instructions to generate the model. In some embodiments, the model includes a first neural network to encode the gathered haptic-based input, and a second neural network to receive the encoded input and supply a sentence based on the encoded input and the previously-gathered haptic-based inputs and the at least one sentence associated with each of the previously-gathered haptic-based inputs.

In some embodiments, the method further includes storing the received text in an electronic record.

According to another aspect, embodiments relate to a system for generating text from a haptic-based input. The system includes an interface for receiving a haptic-based input; and a processor executing instructions stored on a memory and providing a model, wherein the model is configured to at least receive the haptic-based input and supply a text describing the haptic-based input using the interface.

In some embodiments, the haptic-based input is representative of a palpation examination. In some embodiments, the supplied text describes a finding of the palpation examination.

In some embodiments, the system further includes at least one sensor device for gathering the haptic-based input, wherein the at least one sensor device is configured as part of a glove worn by a user.

In some embodiments, the model is trained on previously-gathered haptic-based inputs and at least one sentence associated with each of the previously-gathered haptic-based inputs. In some embodiments, the model includes a first neural network to encode the received haptic-based input, and a second neural network to receive the encoded input and supply a sentence based on the encoded input and the previously-gathered haptic-based inputs and the at least one sentence associated with each of the previously-gathered haptic-based inputs.

In some embodiments, the system further includes one or more databases to store the supplied text in an electronic record.

According to yet another aspect, embodiments relate to a computer readable medium containing computer-executable instructions for a method for generating text from a haptic-based input. The medium includes computer-executable instructions for gathering a haptic-based input using at least one sensor device, computer-executable instructions for providing the haptic-based input to a processor executing instructions stored on a memory and providing a model, and computer-executable instructions for receiving, using an interface, a text describing the gathered haptic-based input.

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

As mentioned previously, clinicians such as doctors, physicians, nurses, or other type of medical personnel often physically examine patients by conducting palpations thereon. Palpation is the process o fusing one's hands to examine another's body. In this process, a clinician touches and feels a patient's body to examine the size, consistency, texture, location, and tenderness of an organ or body part.

After palpation, the clinician may be required to type or otherwise write notes summarizing the palpation findings. However, this post-examination summary step may be susceptible to errors due to lack of memory of the examination, incorrect diagnoses, and mistakes (e.g., typographical errors) made when entering these notes.

There may also be inaccuracies or inconsistencies due to the subjective nature of palpations. For example, one clinician may characterize a portion of a patient's body using one characteristic (e.g., "hard mass"), and another clinician may characterize the same portion of the patient's body by another characteristic (e.g., "soft mass").

The systems and methods described herein rely on a haptic technology-enabled interface combined with a trained model for natural language generation (NLG) to support documentation of findings from PE (e.g., palpation). Embodiments of the systems and methods described herein therefore ensure that accurate information is captured in real-time and provided to the patient's electronic health record (EHR) for better-informed clinical decision-making.

Haptic technology focuses on the implementation of tactile sensors that can compute touch-related parameters (e.g., friction, surface tension, and other resistance forces) and generate force feedback that can be readily interpreted.

While haptic-based technology has been used in a variety of applications, there are limited applications of haptic technology in clinical practice.

In accordance with various embodiments of the systems and methods described herein, a clinician may wear a sensor-embedded glove while physically examining a patient to gather data regarding the patient's body. As the sensors of the glove pass over certain portions of the patient's body, the sensors may generate haptic-based signals based on the characteristics of the respective body portion.

The generated haptic-based signals may be compared to previously-gathered haptic signals and sentences (e.g., words, phrases) associated therewith. Based on the comparison, one or more pieces of text associated with similar haptic signals may be chosen to describe the gathered haptic-based signal. The chosen text may be returned to a clinician and/or stored in the patient's EHR.

Although the present application largely discusses generating text from haptic-based inputs from palpations, the embodiments described herein may be implemented in other applications as well. For example, any type of application in which users use their hands to inspect an item may benefit from the features of the various embodiments described herein.

Figure 1:
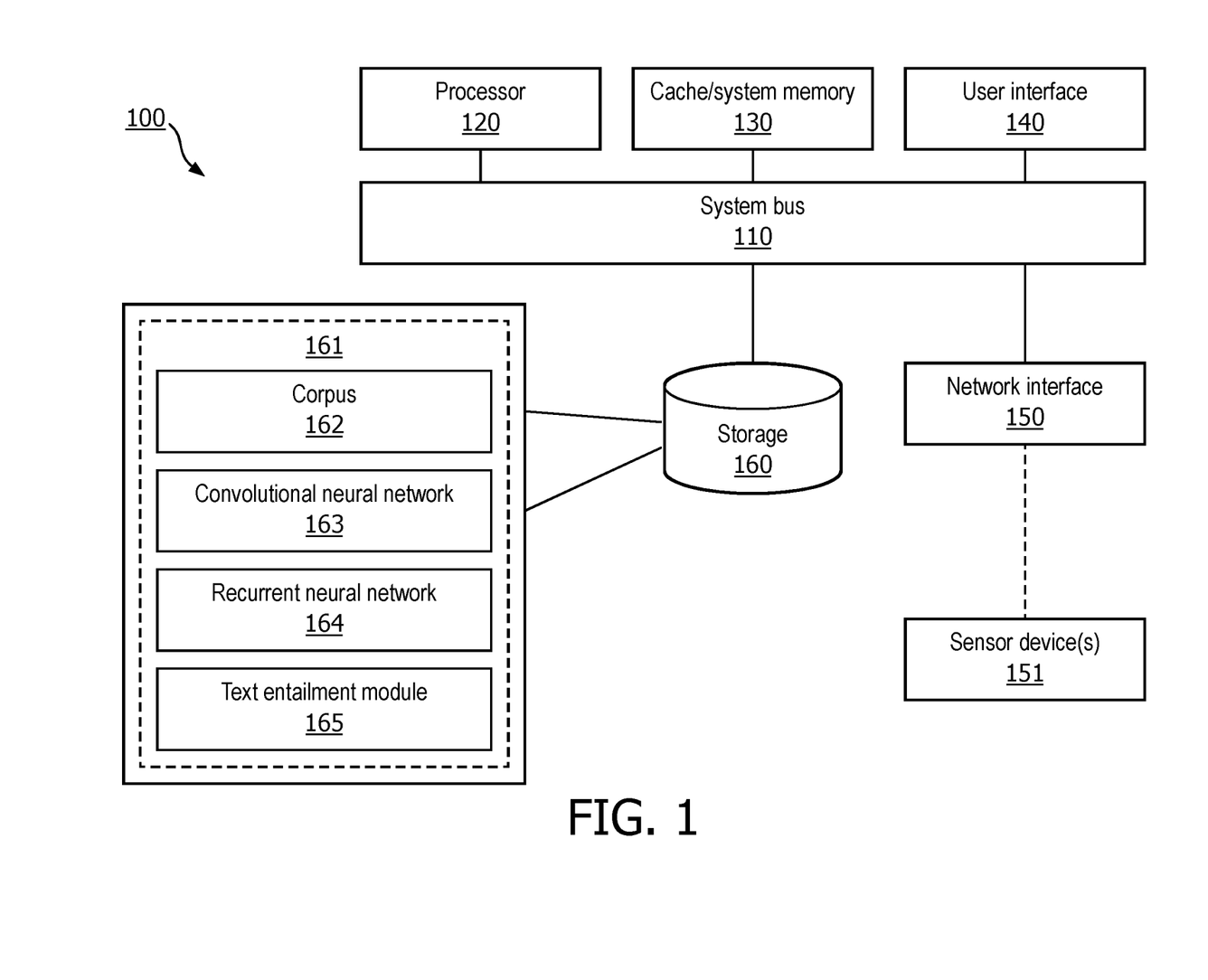
FIG. 1 illustrates a system for generating text from a haptic-based input in accordance with one embodiment.

FIG. 1 illustrates a system 100 for generating text from a haptic-based input in accordance with one embodiment. As shown, the system 100 includes a processor 120, memory 130, a user interface 140, a network interface 150, and storage 160 interconnected via one or more system buses 110. It will be understood that FIG. 1 constitutes, in some respects, an abstraction and that the actual organization of the system 100 and the components thereof may differ from what is illustrated.

The processor 120 may be any hardware device capable of executing instructions stored on memory 130 or storage 160 or otherwise capable of processing data. As such, the processor 120 may include a microprocessor, field programmable gate array (FPGA), application-specific integrated circuit (ASIC), or other similar devices.

The memory 130 may include various memories such as, for example L1, L2, or L3 cache or system memory. As such, the memory 130 may include static random access memory (SRAM), dynamic RAM (DRAM), flash memory, read only memory (ROM), or other similar memory devices. The exact configuration of the memory 130 may vary as long as instructions for generating text from a haptic-based input can be executed.

The user interface 140 may include one or more devices for enabling communication with a user such as a patient or medical personnel. For example, the user interface 140 may include a display, a mouse, and a keyboard for receiving user commands In some embodiments, the user interface 140 may include a command line interface or graphical user interface that may be presented to a remote terminal via the network interface 150.

The user interface 140 may execute on a user device such as a PC, laptop, tablet, mobile device, smartwatch, or the like. The exact configuration of the user interface 140 and the user device on which it executes may vary as along as the features of various embodiments described herein may be accomplished.

The network interface 150 may include one or more devices for enabling communication with other hardware devices. For example, the network interface 150 may include a network interface card (NIC) configured to communicate according to the Ethernet protocol. Additionally, the network interface 150 may implement a TCP/IP stack for communication according to the TCP/IP protocols. Various alternative or additional hardware or configurations for the network interface 150 will be apparent.

The network interface 150 may be in operable communication with one or more sensor devices 151. These sensor devices 151 may be haptic-based (e.g., tactile) sensors configured as part of a glove worn by a clinician when performing a physical examination. Haptic signals may be communicated from the sensor device(s) 151 for analysis by the processor 120 and/or the components of the storage 160.

The sensor devices 151 may be in communication with the system 100 over one or more networks that may link the various components with various types of network connections. The network(s) may be comprised of, or may interface to, any one or more of the Internet, an intranet, a Personal Area Network (PAN), a Local Area Network (LAN), a Wide Area Network (WAN), a Metropolitan Area Network (MAN), a storage area network (SAN), a frame relay connection, an Advanced Intelligent Network (AIN) connection, a synchronous optical network (SONET) connection, a digital T1, T3, E1, or E3 line, a Digital Data Service (DDS) connection, a Digital Subscriber Line (DSL) connection, an Ethernet connection, an Integrated Services Digital Network (ISDN) line, a dial-up port such as a V.90, a V.34, or a V.34bis analog modem connection, a cable modem, an Asynchronous Transfer Mode (ATM) connection, a Fiber Distributed Data Interface (FDDI) connection, a Copper Distributed Data Interface (CDDI) connection, or an optical/DWDM network.

The network or networks may also comprise, include, or interface to any one or more of a Wireless Application Protocol (WAP) link, a Wi-Fi link, a microwave link, a General Packet Radio Service (GPRS) link, a Global System for Mobile Communication G(SM) link, a Code Division Multiple Access (CDMA) link, or a Time Division Multiple access (TDMA) link such as a cellular phone channel, a Global Positioning System (GPS) link, a cellular digital packet data (CDPD) link, a Research in Motion, Limited (RIM) duplex paging type device, a Bluetooth radio link, or an IEEE 802.11-based link.

The storage 160 may include one or more machine-readable storage media such as read-only memory (ROM), random-access memory (RAM), magnetic disk storage media, optical storage media, flash-memory devices, or similar storage media. In various embodiments, the storage 160 may store instructions for execution by the processor 120 or data upon which the processor 120 may operate.

For example, the storage 160 may include or otherwise be configured to execute a model 161 for generating text from a haptic-based input using various components. These components may include a corpus 162, a convolutional neural network 163, a recurrent neural network 164, and a text entailment module 165.

The corpus 162 may include a plurality of training haptic signals and training annotations from palpation. These signals may be gathered previously and annotated with sentences that describe, for example, the geometric and textual properties of the body areas palpated during model training.

The convolutional neural network (CNN) 163 may receive one or more haptic signals from the sensor device(s) 151 that relate to a palpation procedure. The CNN 163 may then encode the received signals into vector representations. The functionality of the CNN 163 may be adjusted by adjusting various parameters such as weight, loss function, optimization approaches, or the like, as would be understood by one skilled in the art.

The recurrent neural network (RNN) 164 may receive the encoded vector representations from the CNN 163, and then supply a sentence based on the encoded vector representations and the previously-gathered haptic-based inputs and sentence(s) associated with each of the previously-gathered haptic-based inputs.

In the context of the present application, the term "sentence" may refer to a word, a group of words, phrases, letter(s), number(s), symbols, or any combination thereof that may be used to describe a result or finding of a palpation.

The text entailment module 165 may receive the sequence of words from the RNN 164 and may employ a unidirectional technique to determine which if any sentences are redundant based on their semantic properties. The text entailment module 165 may be trained on neural embeddings of sentences from the corpus 162. Using an empirical probability threshold, the text entailment module 165 may remove redundant sentences such that the final output is a concise description of the palpation findings.

Figure 2:
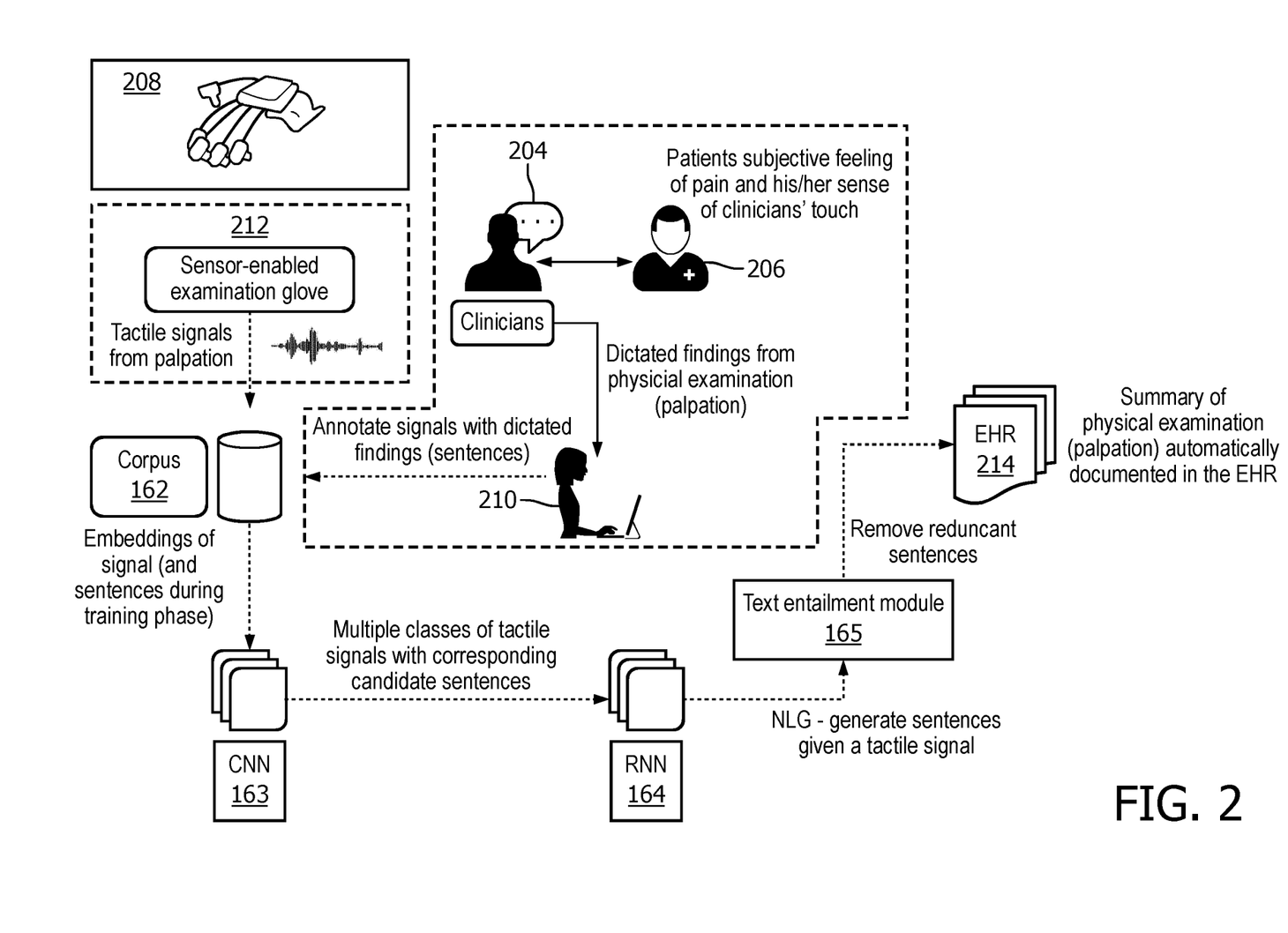
FIG. 2 illustrates a workflow of the components of the system of FIG. 1 in accordance with one embodiment.

FIG. 2 illustrates a workflow 200 of the components of the system 100 of FIG. 1 in accordance with one embodiment. During a training phase 202, one or more clinicians 204 may physically examine a patient 206. As the clinician 204 is physically examining the patient 206 (e.g., performing palpation thereon), the patient 206 may provide their subject feelings of pain and his sense of the clinician's touch. The clinician 204 may also provide their own annotations regarding the palpation.

Haptic signals may be generated based on the palpated portions of a patient's body. For example, a haptic signal may be generated from tactile sensors (e.g., configured as part as a clinician-worn glove 208) as the sensors pass over a patient's body.

Figure 3:
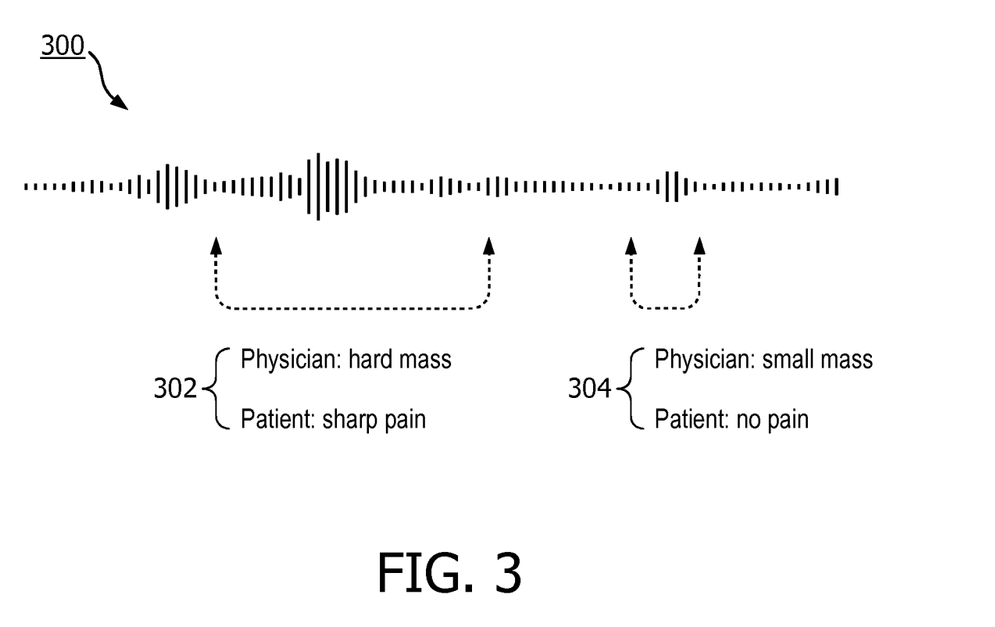
FIG. 3 presents an exemplary haptic signal with annotations in accordance with one embodiment.

FIG. 3, for example, illustrates an exemplary haptic signal 300 obtained from palpation. As can be seen, the signal 300 includes clinician/physician annotations 302 and patient annotations 304 that correspond to portions of the signal 300.

Signals such as the signal 300 may be generated based on detected masses, surfaces with varying friction, and changes in softness of the patient's body. For example, a change in softness as a sensor passes over a ridge near the patient's liver may generate a haptic signal. Signals such as the signal 300, as well as the clinician's annotations 302 and/or the patient's annotations 304, may be communicated to an assistant or other medical personnel 210 for any further dictation.

Referring back to FIG. 2, the corpus 162 may be built from hundreds of these training signals and their corresponding annotations. These may be collected over a period of time and involve examinations conducted by several different clinicians.

The CNN 163 may be trained on the annotated signal-sentence pairs from the corpus 162. During training, the CNN 163 may receive the signal-sentence pairs and convert the pairs into a matrix to represent each pair as numbers.

The CNN 163 may also analyze the received embedded signals to learn or otherwise distinguish various classes of signals. For example, a haptic signal corresponding to an undulated/ill-defined surface may be considerably different from a haptic signal generated by passing a sensor over a circumscribed surface.

Figure 4:
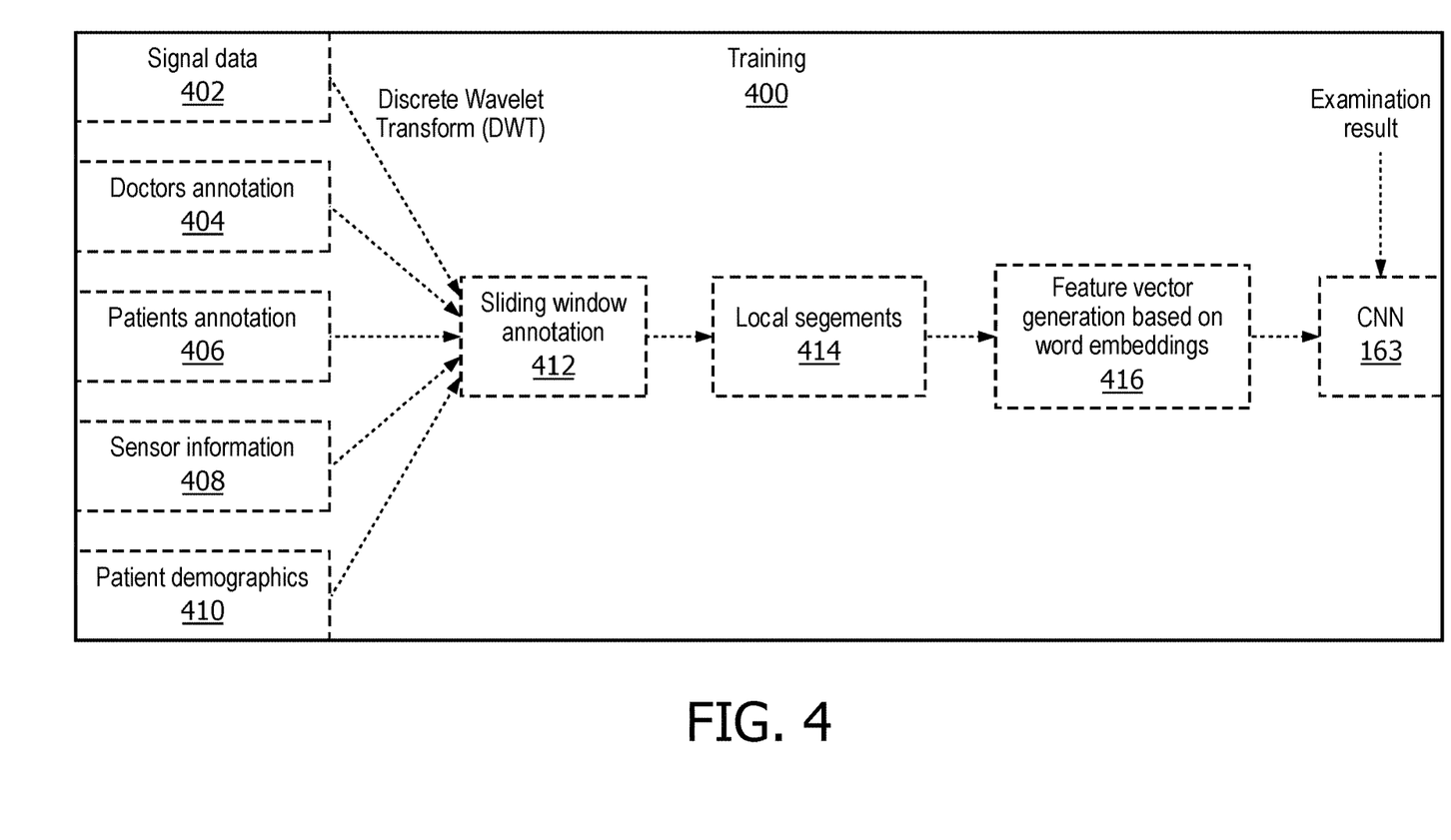
FIG. 4 illustrates a training algorithm in accordance with one embodiment.

FIG. 4 illustrates a model training algorithm 400 in accordance with one embodiment. This algorithm 400 may consider signal data 402 (i.e., the haptic signal(s)), the clinician(s)' annotation(s) 404, the patient's annotation(s) 406, sensor information 408 (e.g., data regarding which sensor of a glove device makes the reading), and data regarding patient demographics 410.

The algorithm 400 may represent the signals using a bag-of-words representation. The algorithm 400 may execute a sliding window procedure 412 in which a window of a certain length is continuously passed over the gathered data to extract a plurality of local segments 414. The algorithm 400 may then generate a feature vector 416 based on word embeddings from each segment using a discrete wavelet transform. The feature vectors 416 may then be supplied to the CNN 163, along with the corresponding embedded signals.

Referring back to FIG. 2, once the model is trained a clinician may conduct tests on a patient and receive a text describing a haptic-based input from the tests. During the testing phase 212, a clinician may gather at least one haptic-based input such as the signal 300 of FIG. 3 using at least one sensor device. The sensor device(s) may be configured as part of glove such as the glove 208, and the gathered haptic-based signals may be communicated to the corpus 162 and the CNN 163.

The CNN 163 may encode the gathered haptic-based input signal from testing to learn a vector representation of the signal. For example, the signal(s) may be transformed into n-gram embeddings, and may be provided to the RNN 164.

The RNN 164 may receive the encoded signals, and then provide a sequence of words that describe the input given to the CNN 163. The provided words may be based on the training signals and their associated sentence(s).

The text entailment module 165 may execute a model (e.g., another neural network) or otherwise rely on various statistical machine learning approaches to provide the text describing the received haptic-based signal. For example, the text entailment module 165 may be trained on neural embeddings of sentences from the corpus 162. The text entailment module 165 may use an empirical probability threshold and remove redundant sentences to therefore provide a concise description of the PE findings.

Figure 5:
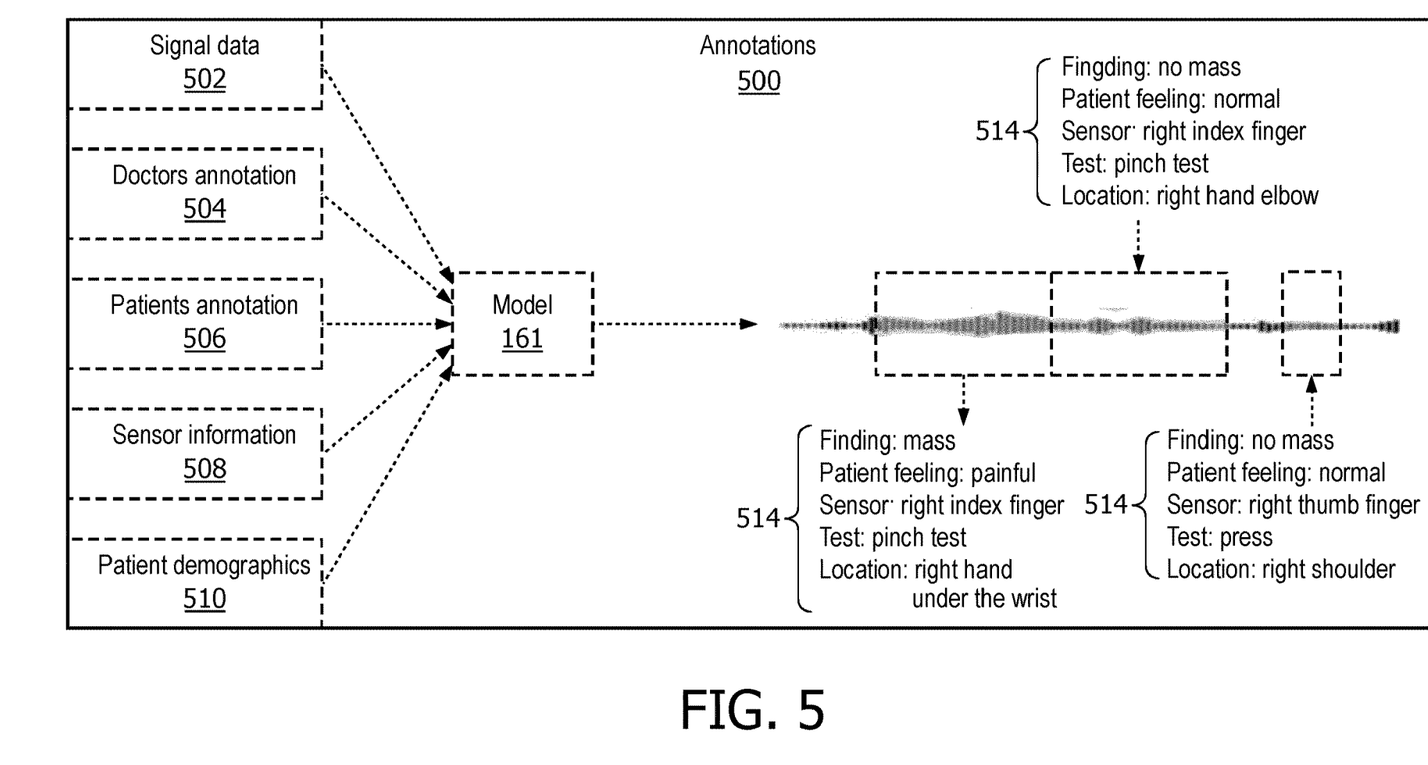
FIG. 5 illustrates an annotation algorithm in accordance with one embodiment.

FIG. 5 illustrates a procedure 500 for annotating a test signal in accordance with one embodiment. As with the training phase, the procedure 500 may consider one or more test signals 502, the clinician's annotation 504, the patient's annotation 506, sensor information 508, and data regarding the patient's demographics 510. This data may be communicated to the now-trained model 161 (which may comprise the CNN 163, the RNN 164, and the text entailment module 165).

The model 161 may provide annotations 514 that describe the received signal data 502 (i.e., the haptic-based input). These annotations/sentences 514 may be communicated to a clinician and/or stored in patient's EHR 214.

Figure 6:
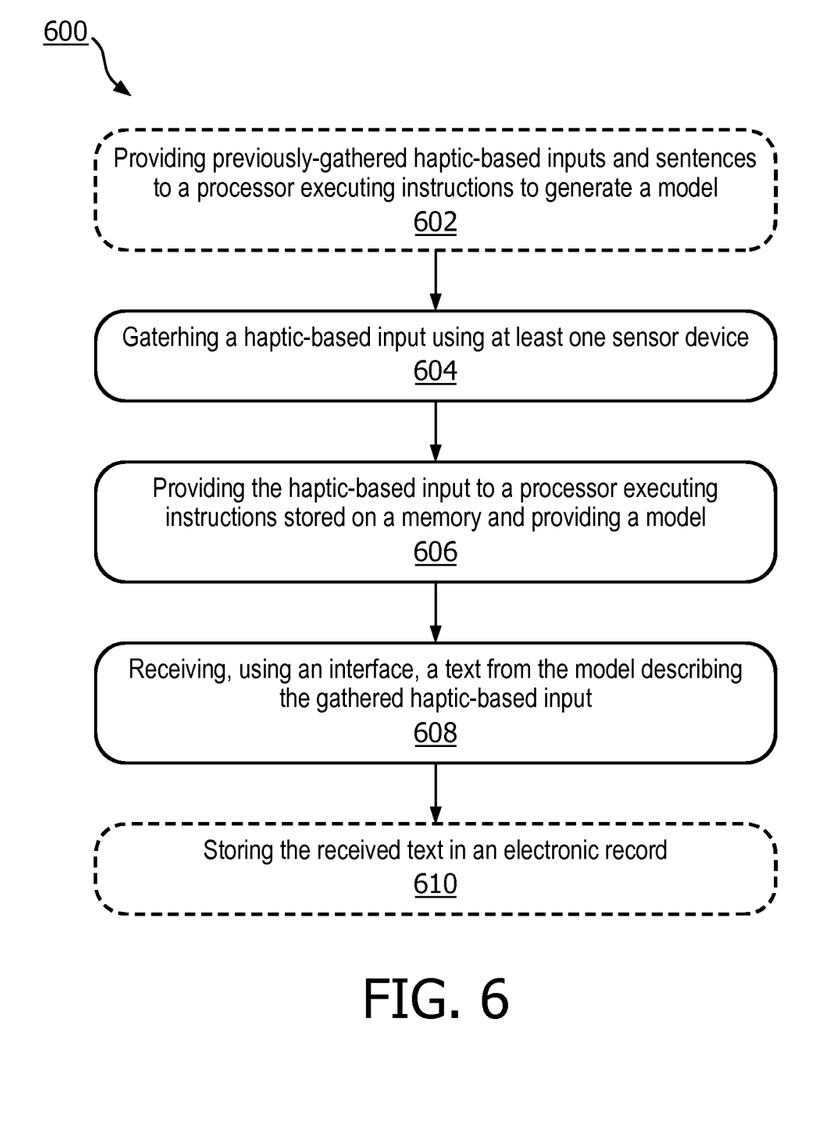
FIG. 6 depicts a flowchart of a method for generating text from a haptic-based input in accordance with one embodiment.

FIG. 6 depicts a flowchart of a method 600 for generating text from a haptic-based input in accordance with one embodiment. Step 602 is optional and involves providing previously-gathered haptic-based inputs and at least one sentence associated with each of the previously-gathered haptic-based inputs to a processor executing instructions stored on a memory to generate a model. These haptic-based inputs may include training haptic signals generated from conducting palpation examinations on patients over the course of a number of training examinations.

During this training phase, a clinician may wear a glove device with tactile sensors configured therewith such as the glove 208 shown in FIG. 2. As the clinician passes these sensors over various portions of the patient's body, certain characteristics of the patient's body may cause different types of haptic signals to be generated.

These previously gathered haptic signals (along with annotations describing the haptic signals) may be used to train a model. Specifically, this model may include or otherwise execute a convolutional neural network and a recurrent neural network such as those described above.

Step 604 involves gathering a haptic-based input using at least one sensor device. This gathered haptic-based input may be related to a palpation examination on a test patient for which a descriptive annotation/text is desired. This haptic-based input may be gathered by a clinician using a sensor-embedded glove such as the glove 208 of FIG. 2.

Step 606 involves providing the haptic-based input to the processor executing instructions stored on the memory and providing the model. The haptic-based input may be transmitted through a wireless hub to a database and also communicated to the processor. The processor may be similar to the processor 120 of FIG. 1, for example.

The model may embed the signal and compare it to the previously-gathered signals and their corresponding sentences. For example, the model may embed the haptic-based input into a vector and compare the vector to the previously gathered, embedded signals (which may each be associated with a sentence).

The model may rank several of the previously-gathered embedded signals based on their similarity to the haptic-based input gathered in step 604. The model may then select a previously gathered signal (along with the corresponding sentence associated with the selected previously gathered signal) based on its similarity to the signal of step 604.

Step 608 involves receiving, using an interface, a text from the model describing the gathered haptic-based input. The received text may be a sentence associated with the selected previously gathered signal in step 606. Accordingly, the received text should describe a finding of the palpation examination. This text may be presented by an interface such as the user interface 140 of FIG. 1, for examination by a clinician.

Step 610 is optional and involves storing the received text in an electronic record. This record may be an electronic health record associated with the patient, for example.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A method for generating text from a haptic-based input, the method comprising:
    gathering a haptic-based input generated by at least one sensor device touching a surface of a body, wherein the haptic-based input indicates at least one characteristic of the body;
    receiving the haptic-based input at a processor executing instructions stored on a memory and providing a model for generating natural language text from the haptic-based input describing the haptic-based input; and
    presenting the text generated by the model describing the gathered haptic-based input to a user via an interface.

2. The method of claim 1 wherein the haptic-based input is representative of a palpation examination.

3. The method of claim 2 wherein the text describes a finding of the palpation examination.

4. The method of claim 1 wherein the at least one sensor device is configured as part of a glove worn by the user.

5. The method of claim 1 further comprising receiving previously-gathered haptic-based inputs and at least one sentence associated with each of the previously-gathered haptic-based inputs to the processor executing instructions to train the model.

6. The method of claim 5 wherein the model comprises:
   a first neural network to encode the gathered haptic-based input, and
   a second neural network to receive the encoded input and supply a sentence based on the encoded input and the previously-gathered haptic-based inputs and the at least one sentence associated with each of the previously-gathered haptic-based inputs.

7. The method of claim 1 further comprising storing the text in an electronic record.

8. A system for generating text from a haptic-based input, the system comprising:
   an interface for receiving a haptic-based input generated by at least one sensor device touching a surface of a body, wherein the haptic-based input indicates at least one characteristic of the body;
   a processor; and
   a non-transitory memory storing a model, wherein when executed by the processor, the model causes to processor to at least:
   receive the haptic-based input from the interface, and
   supply natural language text describing the haptic-based input via a user interface.

9. The system of claim 8 wherein the haptic-based input is representative of a palpation examination.

10. The system of claim 9 wherein the text describes a finding of the palpation examination.

11. The system of claim 8 wherein the at least one sensor device is configured as part of a glove worn by a user.

12. The system of claim 8 wherein the model is trained on previously-gathered haptic-based inputs and at least one sentence associated with each of the previously-gathered haptic-based inputs.

13. The system of claim 12 wherein the model comprises:
   a first neural network to encode the received haptic-based input, and
   a second neural network to receive the encoded input and supply a sentence based on the encoded input and the previously-gathered haptic-based inputs and the at least one sentence associated with each of the previously-gathered haptic-based inputs.

14. The system of claim 8 further comprising one or more databases to store the text in an electronic record.

15. A non-transitory computer readable medium storing computer-executable instructions for generating text from a haptic-based input that, when executed by a processor, cause the processor to:
   receive a haptic-based input generated by at least one sensor device touching a surface of a body, wherein the haptic-based input indicates at least one characteristic of the body;
   apply the haptic-based input to a model to generate natural language text describing the haptic-based input; and
   provide, using an interface, the text describing the haptic-based input.

16. The method of claim 1, wherein the at least one characteristic of the body indicated by the haptic-based input comprises at least one of surface tension, friction or softness of the surface, or a mass beneath the surface.

17. The system of claim 8, wherein the at least one characteristic of the body indicated by the haptic-based input comprises at least one of surface tension, friction or softness of the surface, or a mass beneath the surface.

18. The system of claim 8, wherein the model comprises a corpus, a convolutional neural network, a recurrent neural network, and a text entailment module.

19. The system of claim 18, wherein the recurrent neural network receives encoded vector representations from the convolutional neural network, and supplies a sentence based on the encoded vector representations and previously-gathered haptic-based inputs and sentences associated with the previously-gathered haptic-based inputs, respectively.

20. The non-transitory computer readable medium of claim 15 wherein the model is trained on previously-gathered haptic-based inputs and at least one sentence associated with each of the previously-gathered haptic-based inputs.

* * * * *